(12) United States Patent
Liu et al.

(10) Patent No.: US 10,059,674 B2
(45) Date of Patent: Aug. 28, 2018

(54) DESIGN, SYNTHESIS, AND BIOLOGICAL EVALUATION OF 1-METHYL-1, 4-DIHYRDOINDENO[1,2-C]PYRAZOLE ANALOGUES AS POTENTIAL ANTICANER AGENTS TARGETING TUBULIN COLCHICINE BINDING SITE

(71) Applicant: ACT PHARMA CO., LTD., Jinan Shandong (CN)

(72) Inventors: Zhaopeng Liu, Jinan (CN); Yanna Liu, Jinan (CN); Yanqiu Shi, Jinan (CN); Chengmei Zhang, Jinan (CN)

(73) Assignee: ACT PHARMA CO., LTD., Jinan (CN)

( * ) Notice: Subject to any disclaimer, the term of this patent is extended or adjusted under 35 U.S.C. 154(b) by 0 days.

(21) Appl. No.: 15/152,922

(22) Filed: May 12, 2016

(65) Prior Publication Data

US 2017/0327468 A1    Nov. 16, 2017

(51) Int. Cl.
C07D 231/54    (2006.01)

(52) U.S. Cl.
CPC .................... C07D 231/54 (2013.01)

(58) Field of Classification Search
CPC ................................................... C07D 231/54
See application file for complete search history.

(56) References Cited

FOREIGN PATENT DOCUMENTS

WO    WO 2005095387 A1 * 10/2005  ........... C07D 231/54
WO    WO 2008094896 A1 *  8/2008  ........... C07D 231/54

* cited by examiner

*Primary Examiner* — Sarah Pihonak
*Assistant Examiner* — Jason Deck
(74) *Attorney, Agent, or Firm* — Oliff PLC

(57) ABSTRACT

The invention discloses an indenopyrazole small-molecule tubulin inhibitor, which is characterized by having a structure represented by general formula I:

General Formula I

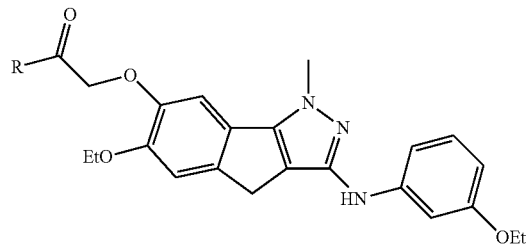

wherein R represents $NH_2$ or NHOH; the invention also discloses a preparation method of the indenopyrazole compound, or pharmaceutical salts thereof. The compound of the present invention is an indenopyrazole small-molecule tubulin inhibitor having a novel structure, and has very strong proliferation inhibition activity to human hepatocellular carcinoma (HepG2) cells, human prostate carcinoma (PC3) cells, human cervical carcinoma (HeLa) cells, human breast adenocarcinoma (MCF-7) cells, and human leukemia (K562) cells; the compound is similar to colchicine in mechanism of action, and thus capable of inhibiting tubulin polymerization; the compound is significant for enhancing the specificity and effectiveness of drugs, reducing toxic and side effects, preventing drug tolerance, and so on.

9 Claims, 2 Drawing Sheets

DESIGN, SYNTHESIS, AND BIOLOGICAL EVALUATION OF 1-METHYL-1, 4-DIHYRDOINDENO[1,2-C]PYRAZOLE ANALOGUES AS POTENTIAL ANTICANER AGENTS TARGETING TUBULIN COLCHICINE BINDING SITE

FIELD OF THE INVENTION

The invention relates to an indenopyrazole small-molecule tubulin inhibitor, a preparation method and application thereof, and belongs to the technical field of chemistry.

BACKGROUND OF THE INVENTION

Microtubules, serving as a major constituent part of a cytoskeleton, are composed of α-tubulin and β-tubulin heterodimers, have dynamic characteristics of polymerization, and depolymerization, and play important roles in such processes as cell morphology maintenance, cell division, signal transduction, and material transport.

Anti-microtubule drugs have already become a major class of chemotherapy drugs, and are widely applied to clinical treatment of various tumors. Tubulin inhibitors affect and interfere with the dynamics of polymerization and depolymerization of the tubulin by binding with specific sites on the tubulin, thereby blocking the formation of M-stage spindles, and arresting the growth of tumor cells at G2/M stage. At present, clinically applied microtubule inhibitors mainly include tubulin depolymerization inhibiting drugs represented by paclitaxel, and tubulin polymerization inhibiting drugs represented by vinblastines. However, the above-mentioned drugs have such problems as great toxic and side effects, easy resulting of drug tolerance, complex structures, and great synthesis difficulty; it has become a hotspot in current anti-tumor drug research to look for novel, high-effect, and low-toxicity microtubule inhibitors.

Hence, designing and synthesizing novel-structure small-molecule tubulin inhibitors is significant for enhancing the specificity and effectiveness of drugs, reducing toxic and side effects, preventing drug tolerance, and so on.

SUMMARY OF THE INVENTION

In view of the above-mentioned shortcomings in the prior art, an object of the present invention is to provide an indenopyrazole small-molecule tubulin inhibitor, and a preparation method thereof.

Another object of the present invention is to provide application of the indenopyrazole small-molecule tubulin inhibitor in preparing anti-tumor drugs.

To achieve the above objects, the following technical solution is adopted in the present invention:

An indenopyrazole small-molecule tubulin inhibitor has a structure represented by general formula I:

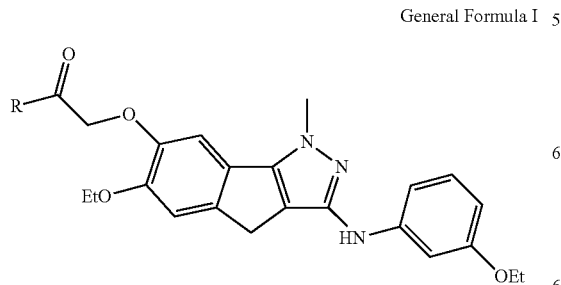

General Formula I wherein R represents $NH_2$ or NHOH.

According to the preparation method of the indenopyrazole small-molecule tubulin inhibitor of the present invention, a synthetic route is as follows:

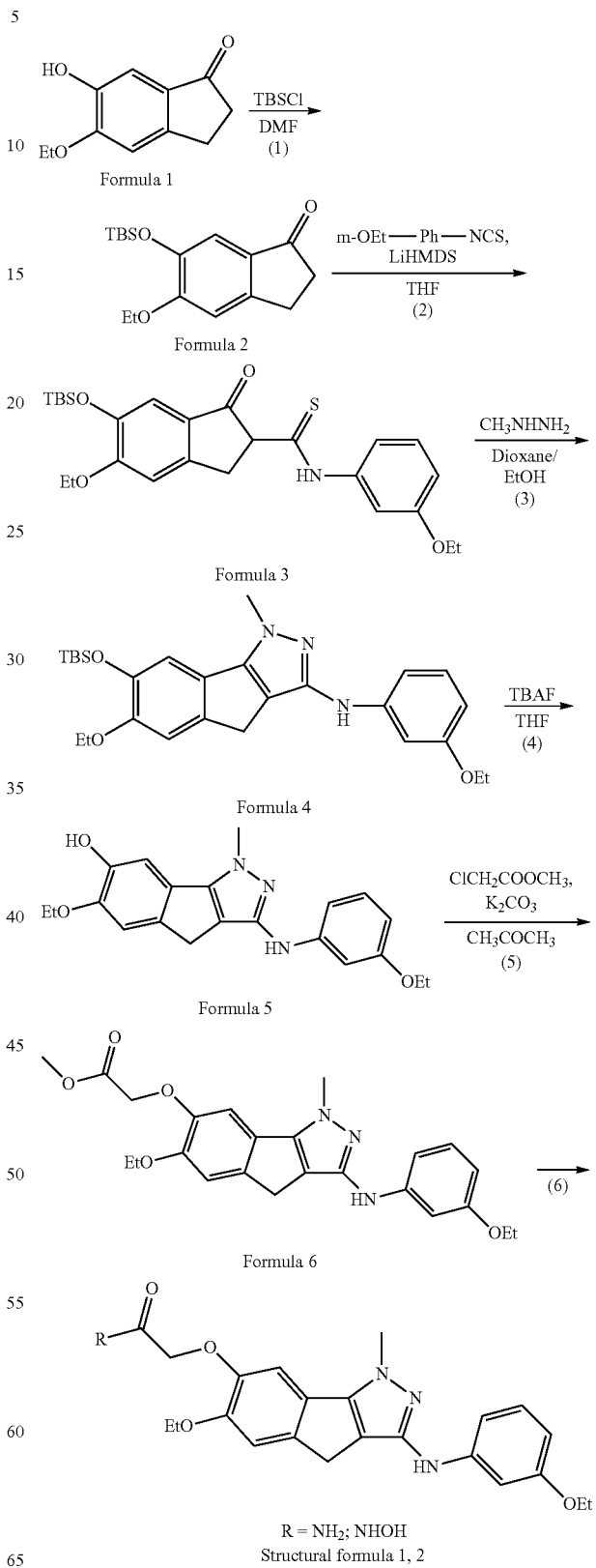

Reagents and conditions: (1) tert-butyldimethylchlorosilane (TBSCl), (2) 3-ethoxyphenylisothiocyanate, and lithium bis(trimethylsilyl) amide (LiHMDS), (3) methylhydrazine, (4) tetrabutylammonium fluoride, (5) methyl chloroacetate, and potassium carbonate, and (6) ammonia water, and hydroxylamine hydrochloride.

Firstly, 5-ethoxy-6-hydroxy-1-indenone (formula 1) is used as a starting raw material, and the 6-hydroxyl group is protected with a tert-butyldimethylsilyl to obtain 5-ethoxy-6-tert-butyldimethylsiloxy-1-indenone (formula 2), wherein a mass ratio of the added 5-ethoxy-6-hydroxy-1-indenone to the added tert-butyldimethylchlorosilane is 3.2:3.76. The compound of formula 2 reacts with the 3-ethoxyphenylisothiocyanate for nucleophilic addition, and then reacts with the methylhydrazine for addition-elimination to obtain a key indenopyrazole; an addition ratio of the 5-ethoxy-6-tert-butyldimethylsiloxy-1-indenone to the 3-ethoxyphenylisothiocyanate to the methylhydrazine is 4.65 g: 3.17 g: 4 mL. The compound of formula 4 reacts, after a protecting group on a 6-hydroxyl group thereof is removed, with the methyl chloroacetate for Williamson ether formation to obtain N-(3-ethoxyphenyl)-1H,4H-6-ethoxy-7-methoxyformylmethoxy-1-methylindeno [1,2-c]pyrazole-3-amine (formula 6), and finally, an ester group side chain on the compound of formula 6 reacts for ammonolysis with different amino substituent groups, thereby obtaining target compounds (structural formula 1, and structural formula 2).

The indenopyrazole small-molecule tubulin inhibitor of the present invention is specifically synthesized through the following steps:

(1) dissolving 5-ethoxy-6-hydroxy-1-indenone into N,N-dimethylformamide, adding imidazole thereto, stirring, and then adding tert-butyldimethylchlorosilane thereto, and stirring; adding citric acid thereto, carrying out cooling, suction filtration, and drying, thereby obtaining 5-ethoxy-6-tert-butyldimethylsiloxy-1-indenone, wherein the mass ratio of the added 5-ethoxy-6-hydroxy-1-indenone to the added imidazole to the added tert-butyldimethylchlorosilane is 12:1.7:3.76;

(2) dissolving the 5-ethoxy-6-tert-butyldimethylsiloxy-1-indenone into anhydrous tetrahydrofuran, performing cooling to −78° C., dropwise adding lithium bis(trimethylsilyl) amide thereto, stirring for 2 h, and then increasing the temperature to −45° C. in 45 min, adding 3-ethoxyphenylisothiocyanate already dissolved into anhydrous tetrahydrofuran thereto, stirring at a room temperature, and placing the mixture over night; adding glacial acetic acid thereto, stirring, removing the solvent by evaporating, and carrying out extracting using dichloromethane, washing, and drying using anhydrous sodium sulfate to obtain a crude product of 5-ethoxy-6-tert-butyldimethylsiloxy-2-(3-ethoxyphenylaminothioformyl)-1-indenone, wherein the mass ratio of the 5-ethoxy-6-tert-butyldimethylsiloxy-1-indenone to the 3-ethoxyphenylisothiocyanate is 4.65:3.17;

(3) dissolving the crude product of 5-ethoxy-6-tert-butyldimethylsiloxy-2-(3-ethoxyphenylaminothioformyl)-1-indenone obtained in step (2) into a mixed solvent of dioxane and ethanol, adding methylhydrazine thereto at 0° C., stirring, and reacting at the room temperature for 84 h; removing the solvent by evaporating, and carrying out column chromatography to obtain N-(3-ethoxyphenyl)-1H,4H-6-ethoxy-7-tert-butyldimethylsiloxy-1-methylindeno [1,2-c]pyrazole-3-amine;

(4) dissolving the N-(3-ethoxyphenyl)-1H,4H-6-ethoxy-7-tert-butyldimethylsiloxy-1-methylindeno [1,2-c]pyrazole-3-amine into tetrahydrofuran, adding tetrabutylammonium fluoride thereto, and stirring; and then carrying out extracting using ethyl acetate, washing, drying using anhydrous sodium sulfate, and column chromatography to obtain N-(3-ethoxyphenyl)-1H,4H-6-ethoxy-7-hydroxy-1-methylindeno [1,2-c]pyrazole-3-amine, wherein the mass ratio of the added N-(3-ethoxyphenyl)-1H,4H-6-ethoxy-7-tert-butyldimethylsiloxy-1-methylindeno [1,2-c]pyrazole-3-amine to the added tetrabutylammonium fluoride is 3.91:2.63;

(5) dissolving the N-(3-ethoxyphenyl)-1H,4H-6-ethoxy-7-hydroxy-1-methylindeno [1,2-c]pyrazole-3-amine into acetone, stirring, adding methyl chloroacetate thereto, reacting at 65° C., and placing the reaction product over night; and then carrying out extracting using ethyl acetate, washing, drying using anhydrous sodium sulfate, and column chromatography to obtain methyl 2-(6-ethoxy-3-(3-ethoxyphenylamino)-1-methyl-1,4-dihydroindeno[1,2-c]pyrazol-7-yl)acetate, wherein the addition ratio of the N-(3-ethoxyphenyl)-1H,4H-6-ethoxy-7-hydroxy-1-methylindeno [1,2-c]pyrazole-3-amine to the methyl chloroacetate is 1.1 g: 0.55 ml;

(6) dissolving the methyl 2-(6-ethoxy-3-(3-ethoxyphenylamino)-1-methyl-1,4-dihydroindeno[1,2-c]pyrazol-7-yl) acetate into methanol, adding ammonia water thereto, and reacting at 65° C. for 12 h to obtain 2-(6-ethoxy-3-(3-ethoxyphenylamino)-1-methyl-1,4-dihydroindeno[1,2-c]pyrazol-7-yl)acetamide (structural formula 1), wherein the addition ratio of the methyl 2-(6-ethoxy-3-(3-ethoxyphenylamino)-1-methyl-1,4-dihydroindeno[1,2-c]pyrazol-7-yl) acetate to the ammonia water is 15 g: 52 mL.

(7) dissolving hydroxylamine hydrochloride into methanol, adding sodium methoxide thereto for neutralization, adding the alcoholic solution of the hydroxylamine to the obtained methanol solution of the methyl 2-(6-ethoxy-3-(3-ethoxyphenylamino)-1-methyl-1,4-dihydroindeno[1,2-c] pyrazol-7-yl)acetate, and reacting at 65° C. for 6 h to obtain 2-(6-ethoxy-3-(3-ethoxyphenylamino)-1-methyl-1,4-dihydroindeno[1,2-c]pyrazol-7-yl)-N-hydroxyacetamide (structural formula 2), wherein a volume ratio of the alcoholic solution of the hydroxylamine to the methanol solution of the methyl 2-(6-ethoxy-3-(3-ethoxyphenylamino)-1-methyl-1,4-dihydroindeno[1,2-c]pyrazol-7-yl)acetate is 1:4.

The structures of the compounds of structural formula 1 and structural formula 2 are as follows:

Structural formula 1

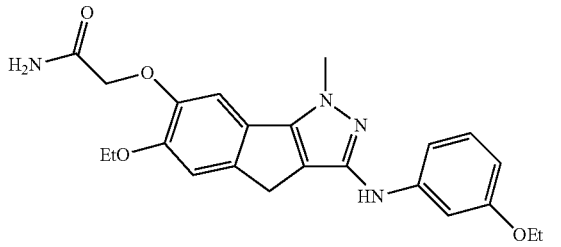

Structural formula 2

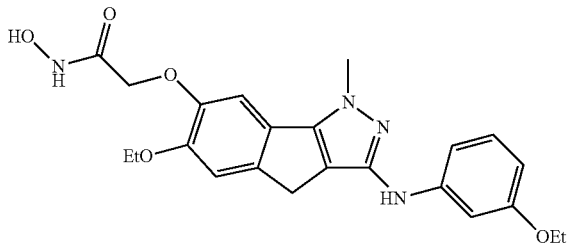

The invention also provides an anti-tumor pharmaceutical preparation containing an effective quantity of the indenopyrazole small-molecule tubulin inhibitor having the structure of general formula I.

The pharmaceutical preparation may be produced with one or more pharmaceutically acceptable carriers and/or excipients into an oral preparation and a parenteral administration preparation, and may be in the form of tablets, pills, capsules, or injection.

The carriers include, for example, normal saline, buffered saline, glucose, water, glycerol, ethanol, or combinations thereof; the excipients can be selected from a group consisting of calcium phosphate, magnesium stearate, talcum powder, dextrin, starch, gel cellulose, methylcellulose, carboxymethylcellulose sodium salt, or polyvinylpyrrolidone.

The present invention has the following beneficial effects:

(1) The tubulin inhibitor designed in the present invention is novel in structure, and is significant for enhancing the specificity and effectiveness of drugs, reducing toxic and side effects, preventing drug tolerance, and so on.

(2) The compounds of the present invention are a novel-structure indenopyrazole small-molecule tubulin inhibitor, which has very strong proliferation inhibition activity to human hepatocellular carcinoma (HepG2) cells, human prostate carcinoma (PC3) cells, human cervical carcinoma (HeLa) cells, human breast adenocarcinoma (MCF-7) cells, and human leukemia (K562) cells; and the compounds are similar to colchicine in mechanism of action, and thus capable of inhibiting tubulin polymerization.

DETAILED DESCRIPTION OF THE EMBODIMENTS

Figure 1:
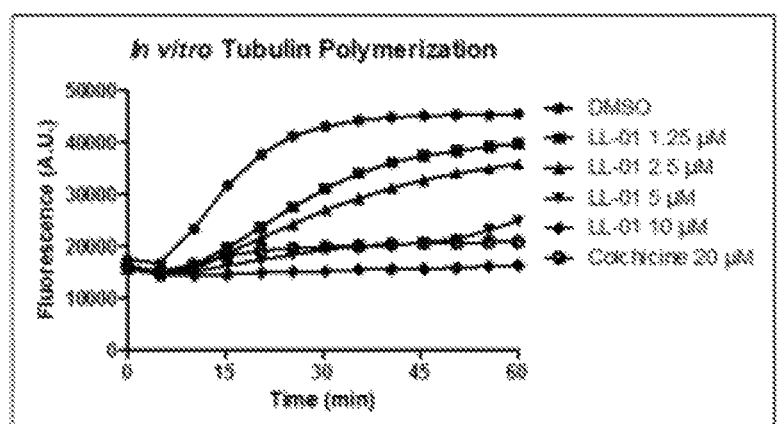
FIG. 1 shows results of a tubulin polymerization experiment of a compound of structural formula 1 in embodiment 4.

The present invention will be further described in conjunction with embodiments. It should be noted that the following descriptions are merely intended to explain the present invention rather than limiting the contents thereof.

Embodiment 1: Preparation of a Compound of Structural Formula 1

(1) 5-ethoxy-6-hydroxy-1-indenone (formula 1) (3.20 g) is dissolved into N,N-dimethylformamide (25 mL), imidazole (1.70 g) is added thereto, and stirred for 5 min, and then tert-butyldimethylehlorosilane (3.76 g) is added thereto, and stirred for 1 h. A citric acid aqueous solution having the mass fraction of 10% is added thereto, and then cooling in a refrigerator, suction filtration, and vacuum drying are carried out, thereby obtaining 5-ethoxy-6-tert-butyldimethylsiloxy-1-indenone (formula 2) (4.65 g), wherein the yield is 91.4%. A melting point ranges from 142° C. to 143° C. ESI-MS m/z 307.5 [MH]$^+$.

(2) The 5-ethoxy-6-tert-butyldimethylsiloxy-1-indenone (formula 2) (4.65 g) is dissolved into anhydrous tetrahydrofuran (60 mL), and cooled to −78° C.; an tetrahydrofuran solution (18.2 mL) of 1M of lithium bis(trimethylsilyl) amide is dropwise added thereto, and stirred for 2 h, and then the temperature is increased to −45° C. in 45 min, 3-ethoxyphenylisothiocyanate (3.17 g) already dissolved into anhydrous tetrahydrofuran (15 mL) is added thereto, and stirred at a room temperature, and then the mixture is placed over night. Glacial acetic acid (2 mL) is added thereto, and stirred for 10 min; the solvent is removed by evaporating, followed by extracting using dichloromethane, washing using 1M of HCl, washing using saturated salt solution, and drying using anhydrous sodium sulfate, such that a crude product of 5-ethoxy-6-tert-butyldimethylsiloxy-2-(3-ethoxyphenylaminothioformyl)-1-indenone (formula 3) is obtained.

(3) The crude product of 5-ethoxy-6-tert-butyldimethylsiloxy-2-(3-ethoxyphenylaminothioformyl)-1-indenone (formula 3) obtained in step (2) is dissolved into a mixed solvent of dioxane and ethanol (100 mL, and in a volume ratio of 1:1), methylhydrazine (4 mL) is added thereto at 0° C., and stirred for 2 h, and a reaction is carried out at the room temperature for 84 h. The solvent is removed by evaporating, and column chromatography is carried out to obtain N-(3-ethoxyphenyl)-1H,4H-6-ethoxy-7-tert-butyldimethylsiloxy-1-methylindeno [1,2-c]pyrazole-3-amine (formula 4) (3.91 g); the total yield of the two steps is 54.1%. The melting point ranges from 110 to 112° C. EST-MS m/z 480.5 [MH]$^+$.

(4) The N-(3-ethoxyphenyl)-1H,4H-6-ethoxy-7-tert-butyldimethylsiloxy-1-methylindeno [1,2-c]pyrazole-3-amine (formula 4) (3.91 g) is dissolved into tetrahydrofuran (70 mL), and tetrabutylammonium fluoride (2.63 g) is added thereto, and stirred for 1 h. Extracting using ethyl acetate, washing using saturated ammonium chloride, washing using saturated salt solution, drying using anhydrous sodium sulfate, evaporating removal of the solvent, and column chromatography are carried out to obtain N-(3 ethoxyphenyl)-1H,4H-6-ethoxy-7-hydroxy-1-methylindeno [1,2-c]pyrazole-3-amine (formula 5) (2.67 g), wherein the yield is 90.67%. The melting point ranges from 153° C. to 155° C. ESI-MS m/z 366.4 [MH]$^+$.

(5) The N-(3-ethoxyphenyl)-1H,4H-6-ethoxy-7-hydroxy-1-methylindeno [1,2-c]pyrazole-3-amine (formula 5) (1.10 g) is dissolved into acetone (35 mL), and stirred for 5 min; methyl chloroacetate (0.55 mL) is added thereto for reacting at 65° C., and then the reaction product is placed over night. Extracting using ethyl acetate, washing using 1M of HCl, washing using water, washing using saturated salt solution, and drying using anhydrous sodium sulfate are carried out. Column chromatography is carried out to obtain methyl 2-(6-ethoxy-3-(3-ethoxyphenylamino)-1-methyl-1,4-dihydroindeno[1,2-c]pyrazol-7-yl)acetate (formula 6) (1.02 g), wherein the yield is 74.1%. The melting point ranges from 139 to 141° C. ESI-MS m/z 438.5 [MH]$^+$.

(6) The methyl 2-(6-ethoxy-3-(3-ethoxyphenylamino)-1-methyl-1,4-dihydroindeno[1,2-c]pyrazol-7-yl)acetate (formula 6) (15.00 g) is dissolved into methanol (50 mL), and ammonia water having the mass concentration of 25% (52 mL) is added thereto for reacting at 65° C. for 12 h to obtain 2-(6-ethoxy-3-(3-ethoxyphenylamino)-1-methyl-1,4-dihydroindeno[1,2-c]pyrazol-7-yl)acetamide (structural formula 1) (11.30 g), wherein the yield is 80.0%. The melting point ranges from 186 to 188° C., ESI-MS m/z 423.4 [MH]$^+$.

Embodiment 2: Preparation of a Compound of Structural Formula 2

(1) 5-ethoxy-6-hydroxy-1-indenone (formula 1) (3.20 g) is dissolved into N,N-dimethylformamide (25 mL), imidazole (1.70 g) is added thereto, and stirred for 5 min, and then tert-butyldimethylchlorosilane (3.76 g) is added thereto, and stirred for 1 h. A citric acid aqueous solution having the mass fraction of 10% is added thereto, and then cooling in a refrigerator, suction filtration, and vacuum drying are carried out, thereby obtaining 5-ethoxy-6-tert-butyldimethylsiloxy-1-indenone (formula 2) (4.65 g), wherein the yield is 91.4%. A melting point ranges from 1423° C. to 143° C. ESI-MS m/z 307.5 [MH]+.

(2) The 5-ethoxy-6-tert-butyldimethylsiloxy-1-indenone (formula 2) (4.65 g) is dissolved into anhydrous tetrahydrofuran (60 mL), and cooled to −78° C.; an tetrahydrofuran solution (18.2 mL) of 1M of lithium bis(trimethylsilyl)amide is dropwise added thereto, and stirred for 2 h, and then the temperature is increased to −45° C. in 45 min, 3-ethoxyphenylisothiocyanate (3.17 g) already dissolved into anhydrous tetrahydrofuran (15 mL) is added thereto, and stirred at a room temperature, and then the mixture is placed over night. Glacial acetic acid (2 mL) is added thereto, and stirred for 10 min; the solvent is removed by evaporating, followed by extracting using dichloromethane, washing using 1M of HCl, washing using saturated salt solution, and drying using anhydrous sodium sulfate, such that a crude product of 5-ethoxy-6-tert-butyldimethylsiloxy-2-(3-ethoxyphenylaminothioformyl)-1-indenone (formula 3) is obtained.

(3) The crude product of 5-ethoxy-6-tert-butyldimethylsiloxy-2-(3-ethoxyphenylaminothioformyl)-1-indenone (formula 3) obtained in step (2) is dissolved into a mixed solvent of dioxane, and ethanol (100 mL, and in a volume ratio of 1:1), methylhydrazine (4 mL) is added thereto at 0° C., and stirred for 2 h, and a reaction is carried out at the room temperature for 84 h. The solvent is removed by evaporating, and column chromatography is carried out to obtain N-(3-ethoxyphenyl)-1H,4H-6-ethoxy-7-tert-butyldimethylsiloxy-1-methylindeno [1,2-c]pyrazole-3-amine (formula 4) (3.91 g); the total yield of the two steps is 54.1%. The melting point ranges from 110° C. to 112° C. ESI-MS m/z 480.5 [MH]+.

(4) The N-(3-ethoxyphenyl)-1H,4H-6-ethoxy-7-tert-butyldimethylsiloxy-1-methylindeno [1,2-c]pyrazole-3-amine (formula 4) (3.91 g) is dissolved into tetrahydrofuran (70 mL), and tetrabutylammonium fluoride (2.63 g) is added thereto, and stirred for 1 h. Extracting using ethyl acetate, washing using saturated ammonium chloride, washing using saturated salt solution, drying using anhydrous sodium sulfate, evaporating removal of the solvent, and column chromatography are carried out to obtain N-(3-ethoxyphenyl)-1H,4H-6-ethoxy-7-hydroxy-1-methylindeno [1,2-c]pyrazole-3-amine (formula 5) (2.67 g), wherein the yield is 90.67%. The melting point ranges from 153° C. to 155° C. ESI-MS m/z 366.4 [MH]+.

(5) The N-(3-ethoxyphenyl)-1H,4H-6-ethoxy-7-hydroxy-1-methylindeno [1,2-c]pyrazole-3-amine (formula 5) (1.10 g) is dissolved into acetone (35 mL), and stirred for 5 min; methyl chloroacetate (0.55 mL) is added thereto for reacting at 65° C., and then the reaction product is placed over night. Extracting using ethyl acetate, washing using 1M of HCl, washing using water, washing using saturated salt solution, and drying using anhydrous sodium sulfate are carried out. Next, column chromatography is carried out to obtain methyl 2-(6-ethoxy-3-(3-ethoxyphenylamino)-1-methyl-1,4-dihydroindeno[1,2-c]pyrazol-7-yl)acetate (formula 6) (1.02 g), wherein the yield is 74.1%. The melting point ranges from 139 to 141° C. ESI-MS m/z 438.5 [MH]+.

(6) Hydroxylamine hydrochloride (1.6 g) is dissolved into methanol, and sodium methoxide having the mass concentration of 28% is added thereto for neutralization; the alcoholic solution of the hydroxylamine is added to the obtained methanol solution of the methyl 2-(6-ethoxy-3-(3-ethoxyphenylamino)-1-methyl-1,4-dihydroindeno[1,2-c]pyrazol-7-yl)acetate (formula 6) (1.00 g) (the volume ratio of the alcoholic solution of the hydroxylamine to the methanol solution of the compound of formula 6 is 1:4) for reacting at 65° C. for 6 h to obtain 2-(6-ethoxy-3-(3-ethoxyphenylamino)-1-methyl-1,4-dihydroindenopyrazol-7-yl)-N-hydroxyacetamide (structural formula 2), wherein the yield is 77.4%. The melting point ranges from 183° C. to 185° C. ESI-MS m/z 439.5 [MH]+.

Embodiment 3: Anti-Proliferation Test

1. Test Method:

The compound of formula 1 (prepared in embodiment 1), and the compound of formula 2 (prepared in embodiment 2) are given at different concentrations to human hepatocellular carcinoma (HepG2) cells, human prostate carcinoma (PC3) cells, human cervical carcinoma (HeLa) cells, human breast adenocarcinoma (MCF-7) cells, and human leukemia (K562) cells; all the groups are incubated 72 h in an incubator containing 5% of $CO_2$ at 37° C., and then inhabitation ratios of the compounds to the tumor cells are measured by using methyl thiazolyl tetrazolium (MTT) colorimetry, and results are shown in table 1.

2. Test Results;

TABLE 1

Inhibition ratios of the Compounds of the Present Invention to Different Tumor Cells

| Compound | $IC_{50}$ (nM) | | | | |
|---|---|---|---|---|---|
| | HepG2 | HeLa | PC3 | K562 | MCF-7 |
| Structural formula 1 | 26.00 | 7.40 | 19.00 | 7.15 | 3.23 |
| Structural formula 2 | 16.40 | 13.20 | 23.50 | 8.33 | 3.36 |

Embodiment 4: Tubulin Polymerization Experiment

1. Experimental drugs: the compound (referred to as LL-01) prepared in embodiment 1, the compound (referred to as LL-02) prepared in embodiment 2, colchicine, and dimethyl sulfoxide (DMSO).

2. Experiment Method:

The tubulin polymerization experiment is carried out according to the specifications of Tubulin Polymerization Assay Kit of Cytoskeleton Corporation.

Figure 2:
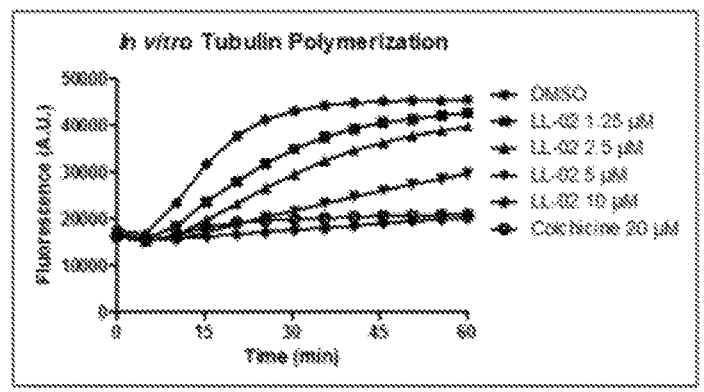
FIG. 2 shows results of a tubulin polymerization experiment of a compound of structural formula 2 in embodiment 4.

3. Results of the experiment are shown in FIGS. 1 and 2, respectively. From FIGS. 1 and 2, it can be seen that the compound prepared in embodiment 1 and the compound prepared in embodiment 2 both are able to inhibit tubulin polymerization, and similar to the colchicine in effect. The tubulin polymerization inhibiting $IC_{50}$ values of compound LL-01 and compound LL-02 are 4.62 μM and 5.33 μM, respectively. Compared with the colchicine, these compounds have more remarkable action effect in inhibiting tubulin polymerization.

Embodiment 5: Non-Clinical Pharmacokinetic Tests—In Vitro Tests

1. Liver Microsomal Metabolism Stability Test (1) Test drugs: the compound (referred to as LL-01) prepared in embodiment 1, the compound (referred to as LL-02) prepared in embodiment 2, and positive controls diphenhydramine powder, dextromethorphan powder, omeprazole powder, and verapamil powder, which all are dissolved by DMSO to 10 mM, respectively, as stock solutions; a phosphate buffer solution (100 mM, pH 7.47); an NADPH regeneration system solution; 100 mM of phosphate buffer solution (pH 7.47) containing 6.5 mM NADP, 16.5 mM G-6-P, 3 U/mLG-6-PD, and 3.3 mM magnesium chloride. It is required to be placed on ice before use; a stop solution: 74 μL of tolbutamide stock solution having the concentration of 10 mM, and 19.3 μL of propranolol stock solution having the concentration of 10 mM are precisely sucked, and added to 1000 mL of acetonitrile for mixing evenly, thereby obtaining an acetonitrile solution containing 200 ng/mL of tolbutamide, and 50 ng/mL of propranolol.

(2) Test method: 3469.5 μL of phosphate buffer solution (pH 7.47) is put into each of three 4 mL centrifugal tubes, and then human, mouse, and rat liver microsomes, each by 112.5 μL, are added to the centrifugal tubes, respectively, and mixed uniformly by means of slight hand shaking to obtain human, mouse, and rat liver microsome dilutions, each having a protein concentration of 0.625 mg/mL, respectively; the dilutions are used for incubation of dextromethorphan, diphenhydramine, omeprazole, and compounds LL-01, LL-02 to be measured, respectively.

2698.5 μL of phosphate buffer solution (pH 7.47) is put into each of two 4 mL centrifugal tubes, and then dog and monkey liver microsomes, each by 87.5 μL, are added to the centrifugal tubes, respectively, and mixed uniformly by means of slight hand shaking to obtain dog and monkey liver microsome dilutions, each having the protein concentration of 0.625 mg/mL, respectively; the dilutions are used for incubation of compounds LL-01, LL-02 to be measured, respectively.

1181μ of phosphate buffer solution (pH 7.47) is put into each of two 4 mL centrifugal tubes, and then dog, and monkey liver microsomes, each by 19 μL, are added to the centrifugal tubes, respectively, and mixed uniformly by means of slight hand shaking to obtain dog and monkey liver microsome dilutions, each having the protein concentration of 0.3125 mg/mL, respectively; the dilutions are used for incubation of verapamil, respectively.

The human, mouse, rat, dog, and monkey liver microsomes, each by 398 μL, are added into a 96-hole incubation plate (N=2), and 0.25 mM working solutions of dextromethorphan, diphenhydramine, omeprazole, verapamil, LL-01, and LL-02, each by 2 μL, are added thereto, and mixed evenly.

A new 96-hole deep-hole plate is utilized, and 300 μL of precooled stop solution is added into each hole; and then the deep-hole plate is placed on ice to serve as a stop plate.

The 96-hole incubation plate, and the NADPH regeneration system are placed into a water bath case at 37° C., vibrated at 100 r/min, and pre-incubated 5 min. 80 μL of incubation solution is taken out of each hole of the incubation plate, and added to the stop plate, and then 20 μL of NADPH regeneration system solution is further added thereto, and mixed evenly to serve as a 0 min sample. Subsequently, 80 μL of NADPH regeneration system solution is added into each hole of the incubation plate to initiate reaction, and timing is started. The protein concentration of each of dextromethorphan, diphenhydramine, omeprazole, LL-01, and LL-02 is 0.5 mg/mL, while the protein concentration of verapamil is 0.25 mg/mL.

100 μL of reaction solution is taken at each of 10, 30, and 90 min points of the reaction, and added to the stop plate, and vibration is carried out for 5 min to stop the reaction. The stop plate is centrifuged for 10 min under the conditions of 5000× g, and 4° C. 100 μL of supernatant is taken, added to a 96-hole plate into which 200 μL of distilled water is added in advance, and mixed evenly; sample analysis is carried out by means of LC-MS/M.

Data calculation: a drawing is plotted by using natural logarithms of percentages of remainders of the compounds, and time, and $T_{1/2}$, and $C_{Lint}$ are calculated according to the following formulas, wherein V/M is equal to 1/protein concentration.

$$T_{1/2} = \frac{0.693}{-\text{slope}} \quad CL_{int} = \frac{0.693}{T_{1/2}} \cdot \frac{V}{M}$$

(3) Test Results:

Results of the metabolism stability tests of the positive controls in corresponding various categories are shown in table 2.

TABLE 2

Half-Life Periods, and Intrinsic Clearance Rates of Positive Controls in In Vitro Incubation Systems

| Category | Compound | dextromethorphan | diphenhydramine | omeprazole | verapamil |
|---|---|---|---|---|---|
| Human | $T_{1/2}$ (min) | 55.7 | NA | NA | NA |
|  | $CL_{int}$ (μL/min/mg) | 24.9 | NA | NA | NA |
| Mouse | $T_{1/2}$ (min) | NA | 49.6 | NA | NA |
|  | $CL_{int}$ (μL/min/mg) | NA | 27.9 | NA | NA |
| Rat | $T_{1/2}$ (min) | NA | NA | 15.7 | NA |
|  | $CL_{int}$ (μL/min/mg) | NA | NA | 88.3 | NA |
| Dog | $T_{1/2}$ (min) | NA | NA | NA | 25.8 |
|  | $CL_{int}$ (μL/min/mg) | NA | NA | NA | 107.6 |
| Monkey | $T_{1/2}$ (min) | NA | NA | NA | 4.6 |
|  | $CL_{int}$ (μL/min/mg) | NA | NA | NA | 603.1 |

From table 2, it can be seen that the positive controls all are metabolized normally in the liver microsomes of various categories; this experimental system may be used to verify the in vitro metabolism stability of compounds LL-01, LL-02 to be measured. Results of the metabolism stability of the compounds to be measured are shown in table 3.

TABLE 3

Half-Life Periods, and Intrinsic Clearance Rates of Compounds LL-01, LL-02 to be measured in In Vitro Incubation Systems

| Category | Compound | LL-01 | LL-02 |
|---|---|---|---|
| Human | $T_{1/2}$ (min) | 44.7 | 12.9 |
|  | $CL_{int}$ (μL/min/mg) | 31.0 | 107.8 |
| Mouse | $T_{1/2}$ (min) | 55.3 | 17.8 |
|  | $CL_{int}$ (μL/min/mg) | 25.0 | 78.0 |
| Rat | $T_{1/2}$ (min) | 56.8 | 24.0 |
|  | $CL_{int}$ (μL/min/mg) | 24.4 | 57.7 |
| Dog | $T_{1/2}$ (min) | 24.7 | 7.5 |
|  | $CL_{int}$ (μL/min/mg) | 56.0 | 184.8 |
| Monkey | $T_{1/2}$ (min) | 21.6 | 1.3 |
|  | $CL_{int}$ (μL/min/mg) | 64.2 | 1069.8 |

The corresponding remainder percentages of compound LL-01 at specific incubation time are shown in table 4.

TABLE 4

Remainder (%) of LL-01 after the Incubation of Human,
Mouse, Rat, Dog, and Monkey Liver Microsomes

| | LL-01 Remainder (%) | | | | |
|---|---|---|---|---|---|
| Incubation time (min) | Human | Mouse | Rat | Dog | Monkey |
| 0 | 100.00 | 100.00 | 100.00 | 100.00 | 100.00 |
| 10 | 78.76 | 87.76 | 87.70 | 74.20 | 52.00 |
| 30 | 56.18 | 63.76 | 68.13 | 38.61 | 20.40 |
| 90 | 23.87 | 32.23 | 33.19 | 7.93 | 4.76 |

The test results indicate that the metabolism of LL-01 is faster in the liver microsomes of dog, and moderate in the liver microsomes of human, mouse, rat, and monkey; and the metabolism of LL-02 is moderate in the liver microsomes of rat, and faster in the liver microsomes of human, mouse, dog, and monkey.

2. MDCK Cell Permeability Test (1) Test drugs: the compound (referred to as LL-01) prepared in embodiment 1, the compound (referred to as LL-02) prepared in embodiment 2, and cyclosporine A, which are dissolved by using appropriate volumes of DMSO to obtain an LL-01 stock solution, an LL-02 stock solution, and a cyclosporine A stock solution, each having the concentration of 10 mM; positive control: amprenavir, which is dissolved by using an appropriate volume of DMSO, and mixed evenly to obtain a positive control stock solution having the concentration of 3 mM; a certain quantity of sodium fluorescein is weighed precisely, dissolved by using an appropriate volume of distilled water, and mixed evenly to obtain a sodium fluorescein stock solution having the concentration of 50 mM; a phosphate buffer solution (0.01M, and pH 7.47); a stop solution: 74 µL of tolbutamide stock solution having the concentration of 10 mM, and 19.3 µL of propranolol stock solution having the concentration of 10 mM are precisely sucked, and added to 1000 mL of acetonitrile for mixing evenly, thereby obtaining an acetonitrile solution containing 200 ng/mL of tolbutamide, and 50 ng/mL of propranolol.

(2) Test method: a cell attachment condition is checked on the first day of cell culture; when attachment reaches 80%-90% of a bottom surface of a culture flask, a culture solution is removed, and 5 mL of preheated 10 mM phosphate buffer solution is added into the culture flask; the culture flask is shaken slightly, and then the buffer solution in the flask is removed by means of suction. Subsequently, 3 mL of preheated pancreatin is added thereto, and the culture flask is placed into a $CO_2$ incubator at 37° C. for cell dissociation; after complete cell dissociation, 7 mL of complete culture solution DMEM containing phenol red is added thereto to stop dissociation, and uniform blowing, and beating should be carried out. It is transferred to a 50 mL centrifugal tube, and centrifuged at 900 rpm for 3 min; the supernatant is removed, and then the remainder is diluted by using the complete culture solution DMEM containing phenol red, and mixed evenly, and cells are counted. Subsequently, the cell concentration is diluted by using the complete culture solution DMEM to $2\times10^5$/mL. Two 24-hole plates are utilized, and 0.3 mL of $2\times10^5$/mL cell solution is added to side A of each hole, while 1 mL of complete culture solution DMEM is added to side B of the same.

After 24 h of cell culture, the culture solution on sides A and B is removed, and fresh complete culture solution DMEM is added to sides A and B by 0.3 mL, and 1 mL, respectively, and culture is continued.

On the fourth day of cell culture, DMEM without phenol red is added to two 50 mL centrifugal tubes by 26 mL and 18 mL, respectively, and then 13 µL of sodium fluorescein, and 18 µL of cyclosporine A are added thereto, respectively, and mixed evenly, thereby obtaining a sodium fluorescein dilution having the concentration of 25 µM, and a cyclosporine A dilution having the concentration of 10 µM, respectively; the two dilutions are used for dosage, and pre-incubation of amprenavir and compounds LL-01 and LL-02 to be measured, respectively.

6 mL of 25 µM sodium fluorescein dilution is put into each of four 10 mL EP tubes, and then 3 mM amprenavir, 10 mM DMBT, 10 mM LL-01, and 10 mM LL-02 are added, each by 6 µL, to the EP tubes, respectively, and mixed evenly; 3 ml of mixed solution is correspondingly added to each of the EP tubes; finally, 3 µL of 10 mM of cyclosporine A is added into each tube, and mixed evenly, and therefore, corresponding incubation working solutions, namely doses, of the positive control amprenavir, and compounds LL-01, and LL-02 to be measured are obtained.

Liquids on both sides A and B are removed by means of suction, and the phosphate buffer solution is added to sides A and B by 0.3 mL, and 1 mL, respectively, for cleaning 30 min.

After cleaning, DMEM without phenol red is added to both sides A and B of odd-numbered lines by 0.2 mL, and 0.7 mL, respectively. DMEM containing 10 µM cyclosporine A without phenol red is added to both sides A and B of even-numbered lines by 0.2 mL, and 0.7 mL, respectively. Pre-incubation is carried out for 40 min.

After completion of the pre-incubation, liquids on both sides are removed by means of suction. For transport from side A to side B, 0.2 mL of compounds to be measured or positive control is added to side A, while 0.7 mL of DMEM is added to side B to serve as an accepting side; from side B to side A, 0.7 mL of compounds to be measured or positive control is added to side B, while 0.2 mL of DMEM is added to side A to serve as the accepting side. Incubation is carried out in the incubator for 90 min.

After completion of the incubation, 190 µL of liquid is sucked from each of both sides A and B of each hole and the doses into a 96-hole shallow-hole plate for backup.

A new 96-hole deep-hole plate is utilized, and 180 µL of precooled precipitant is added into each hole, and then the deep-hole plate is placed on ice to serve as a precipitation plate.

The backup sample of the 96-hole shallow-hole plate is taken by 60 µL, added into the precipitation plate, and vibrated 5 min for mixing evenly.

The precipitation plate is centrifuged 10 min under the conditions of 5000× g, and 4° C. 100 µL of supernatant is shifted to a 96-hole plate into which 200 µL of distilled water is added in advance, and mixed evenly, and then sample analysis is carried out by means of LC-MS/MS.

Data calculation: apparent permeability coefficients Papp are measured by comparing unit time remainders of the compounds with the doses, and a bottom area, thereby knowing the permeation conditions of drugs, and whether the drugs are P-gp substrates is judged by calculating a ratio of Papp (B→A) to Papp (A→B), i.e., an Efflux ratio, in the absence of a P-gp inhibitor, and according to the following formulas, wherein dO/dt represents a permeation rate, $C_0$ represents an initial concentration of each compound, and A represents the surface area of the cell monolayer.

$$Papp=(dQ/dt)\times(1/C0)\times(1/A)$$

$$\text{Efflux ratio}=Papp(B\rightarrow A)/Papp(A\rightarrow B)$$

(3) Test Results:

The apparent permeability coefficients of the positive control, the recovery rates of the incubation sample, the Efflux ratio results, and judgment of permeability, and substrate are shown in table 5.

TABLE 5

Permeability Results of the Positive Control

| Com- pound | Recovery rate | | Apparent permeability coefficient ($\times 10^{-6}$ cm/s) | | Efflux ratio | Permeability Judgment | PGP substrate judgment |
|---|---|---|---|---|---|---|---|
| | A→B | B→A | A→B | B→A | | | |
| Ampre- navir | 106.4 95.4 | 101.9 100.0 | 5.42 33.40 | 75.48 22.56 | 13.9 0.7 | High permeability | Yes |

Data has consistency in contrast with the historical data range of this laboratory, indicating that the experimental system may be used to verify the cell permeability transport conditions of compounds LL-01, and LL-02 to be measured. Relevant results of the compounds to be measured are shown in table 6.

TABLE 6

Permeability Results of Compounds LL-01, and LL-02 To Be Measured

| Com- pound | Recovery rate | | Apparent permeability coefficient ($\times 10^{-6}$ cm/s) | | Efflux ratio | Permeability Judgment | PGP substrate judgment |
|---|---|---|---|---|---|---|---|
| | A→B | B→A | A→B | B→A | | | |
| LL-01 | 93.8 69.4 62.3 | 101.5 85.4 84.6 | 0.6 16.0 18.0 | 0.8 18.9 19.6 | 1.2 1.2 1.1 | Moderate permeability | No |
| LL-02 | 89.4 59.2 | 91.3 79.4 | 7.4 12.4 | 32.6 6.9 | 4.4 0.6 | Moderate permeability | Yes |

Test results indicate that the compound LL-02 has moderate permeability in MDCK cells, and is the PGP substrate. LL-01 has moderate permeability in MDCK cells, and is not the PGP substrate.

Embodiment 6: in Vivo Test

1. Test article: the compound (referred to as LL-01) prepared in embodiment 1

2. Test animal: SD rats, which are 284-304 g before the test, and bought from Shanghai Xipuer-Bikai laboratory animal Co., Ltd. with production license No. SCXK (Hu) 2013-0016, and laboratory animal certificate Nos. 2008001658223 and 2008001658296.

3. Test method:

(1) Preparation of a Solvent:

PBS preparation: 4.01 g of NaCl, 100.04 mg of KCl, 1.83 g of $Na_2HPO_4 \cdot 12H_2O$, and 120.32 mg of $KH_2PO_4$ are weighed, while 500 mL of water measured, and all the materials are put into a glass bottle, and mixed evenly by means of vibration, and then put into cold storage for later use. The solvent is numbered 20160224-QYZ-01.

(2) Preparation of Test Substances:

2.85 mg of compound LL-01 is weighed, and then put into a glass bottle; 0.687 mL of DMSO is added into the glass bottle, and ultrasonic treatment is carried out for 2 min; next, 2.062 mL of Solutol HS 15 is added thereto, and ultrasonic treatment is carried out for 4 min; and then 10.995 mL of PBS is added thereto, and ultrasonic treatment is carried out for 8 min after eddying. This test substance is numbered 20160324-RW-01, 12.74 mg of compound LL-01 is weighed, and then put into a glass bottle; 0.614 mL of DMSO is added into the glass bottle, and ultrasonic treatment is carried out for 2 min; next, 1.843 mL of Solutol HS 15 is added thereto, and ultrasonic treatment is carried out for 4 min; and then 9.830 mL of PBS is added thereto, and ultrasonic treatment is carried out for 8 min after eddying. This test substance is numbered 20160324-RW-02, (3) Administration of the Test Substances:

The dosage of intravenous administration is 1 mg/kg, while the dosage of oral administration is 10 mg/kg. A night of fasting is required before administration, and feeding should be carried out 4 hours later after administration. Detailed animal weights and dosages are shown in table 7.

TABLE 7

Animal Weights, and Dosages

| Test substance | Animal test No. | Weight (g) | Method of administration | Volume of administration (mL) |
|---|---|---|---|---|
| LL-01 | 101 | 276 | IV | 1.38 |
| | 102 | 270 | IV | 1.35 |
| | 103 | 280 | IV | 1.40 |
| LL-01 | 201 | 276 | PO | 2.76 |
| | 202 | 296 | PO | 2.96 |
| | 203 | 292 | PO | 2.92 |

(4) Collection, and Detection of Samples:

Blood is collected (about 150-200 uL) at every time points of 0.083 (only vein), 0.25, 0.5, 1, 2, 4, 8, and 24 hours after administration through orbital venous plexus puncture into $EDTA-K_2$ (20%, and 2 µL) anticoagulant tubes, respectively; the blood samples are centrifuged 8 min at 6000 rpm in 1 h (placed on wet ice before being centrifuged), and the supernatant, namely blood plasma is put into $-20°$ C. low-temperature conservation for LC-MS/MS analysis later.

The content of compound LL-01 in SD rat blood plasma is detected by use of LC-MS/MS method.

(5) Data Processing:

Computer program Microsoft Office Excel 2007 (Microsoft, USA) is used for data processing, and drawing. A statistical moment method of WinNolin 6.4 processing software is used to calculate pharmacokinetic parameters.

4. Test Results:

Results of the drug concentrations (ng/mL) in the blood plasma samples of SD rats after intravenous administration of LL-01 thereto by 1 mg/kg are shown in table 8:

TABLE 8

Drug Concentrations (ng/mL) in the Blood Plasma Samples of SD Rats after Intravenous Administration of LL-01 thereto by 1 mg/Kg

| Time (h) | 101M | 102M | 103M | Mean | Standard deviation |
|---|---|---|---|---|---|
| 0.08 | 2721.3 | 2401.2 | 2688.2 | 2603.6 | 176.0 |
| 0.25 | 2015.6 | 1920.7 | 1914.1 | 1950.1 | 56.8 |
| 0.5 | 1760.4 | 1392.5 | 1724.9 | 1625.9 | 202.9 |
| 1 | 875.8 | 842.0 | 933.9 | 883.9 | 46.5 |
| 2 | 398.2 | 372.4 | 511.8 | 427.5 | 74.2 |

TABLE 8-continued

Drug Concentrations (ng/mL) in the Blood Plasma Samples of SD Rats after Intravenous Administration of LL-01 thereto by 1 mg/Kg

| Time (h) | 101M | 102M | 103M | Mean | Standard deviation |
|---|---|---|---|---|---|
| 4 | 87.6 | 67.1 | 92.8 | 82.5 | 13.6 |
| 8 | 8.6 | 9.1 | 5.6 | 7.8 | 1.9 |
| 24 | BLQ | BLQ | BLQ | NA | NA |

Results of the drug concentrations (ng/mL) in the blood plasma samples of SD rats after oral administration of LL-01 thereto by 10 mg/kg are shown in table 9:

TABLE 9

Drug Concentrations (ng/mL) in the Blood Plasma Samples of SD Rats after Oral Administration of LL-01 Thereto By 10 mg/Kg

| Time (h) | 201M | 202M | 203M | Mean | Standard deviation |
|---|---|---|---|---|---|
| 0.25 | 158.6 | 466.5 | 216.2 | 280.4 | 163.7 |
| 0.5 | 374.4 | 959.0 | 339.3 | 557.6 | 348.1 |
| 1 | 869.2 | 1103.8 | 777.7 | 916.9 | 168.2 |
| 2 | 674.7 | 1283.3 | 801.0 | 919.7 | 321.2 |
| 4 | 1308.5 | 1717.3 | 813.5 | 1279.8 | 452.6 |
| 8 | 451.0 | 916.0 | 445.9 | 604.3 | 270.0 |
| 24 | 46.8 | 17.4 | 16.6 | 26.9 | 17.2 |

Results of non-atrioventricular pharmacokinetic parameters of male SD rats after single intravenous administration of LL-01 (1 mg/kg) thereto are shown in table 10:

TABLE 10

Non-Atrioventricular Pharmacokinetic Parameters of Male SD Rats After Single Intravenous Administration of LL-01 (1 mg/kg) Thereto

| PK parameter | 101M | 102M | 103M | Mean | Standard deviation |
|---|---|---|---|---|---|
| HL_Lambda_z (hr) | 1.06 | 1.00 | 0.94 | 1.00 | 0.06 |
| $T_{max}$ (hr) | 0.08 | 0.08 | 0.08 | 0.08 | 0.00 |
| $C_{max}$ (ng/mL) | 2721.3 | 2401.2 | 2688.2 | 2603.6 | 176.0 |
| $AUC_{last}$ (hr*ng/mL) | 3085.8 | 2743.7 | 3271.8 | 3033.8 | 267.8 |
| $AUC_{INF\_pred}$ (hr*ng/mL) | 3097.8 | 2753.8 | 3279.1 | 3043.6 | 266.8 |
| $MRT_{INF\_pred}$ (hr) | 1.17 | 1.16 | 1.21 | 1.18 | 0.03 |
| $Vz_{\_pred}$ (L/kg) | 0.49 | 0.53 | 0.41 | 0.48 | 0.06 |
| $Cl_{\_pred}$ (L/hr/kg) | 0.32 | 0.36 | 0.30 | 0.33 | 0.03 |
| λz Calculation Time Range (hr) | 1-8 | 0.25-8 | 1-8 | NA | NA |

Results of non-atrioventricular pharmacokinetic parameters of male SD rats after single oral administration of LL-01 (10 mg/kg) thereto are shown in table 11:

TABLE 11

Non-Atrioventricular Pharmacokinetic Parameters of Male SD Rats After Single Oral Administration of LL-01 (10 mg/kg) Thereto

| PK parameter | 201M | 202M | 203M | Mean | Standard deviation |
|---|---|---|---|---|---|
| HL_Lambda_z (hr) | 4.35 | 2.95 | 3.50 | 3.60 | 0.70 |
| $T_{max}$ (hr) | 4.00 | 4.00 | 4.00 | 4.00 | 0.00 |
| $C_{max}$ (ng/mL) | 1308.5 | 1717.3 | 813.5 | 1279.8 | 452.6 |
| $AUC_{last}$ (hr*ng/mL) | 10653.9 | 17680.2 | 8998.4 | 12444.1 | 4609.5 |
| $AUC_{INF\_pred}$ (hr*ng/mL) | 10933.9 | 17756.9 | 9084.1 | 12591.6 | 4567.9 |
| $MRT_{INF\_pred}$ (hr) | 6.58 | 5.87 | 5.96 | 6.14 | 0.39 |
| $Vz_{\_F\_pred}$ (L/kg) | 5.74 | 2.40 | 5.57 | 4.57 | 1.88 |
| $Cl_{\_F\_pred}$ (L/hr/kg) | 0.91 | 0.56 | 1.10 | 0.86 | 0.27 |
| λz Calculation Time Range (hr) | 4-24 | 4-24 | 4-24 | NA | NA |
| F(%) | 35.12 | 58.28 | 29.66 | 41.02 | 15.19 |

Figure 3:
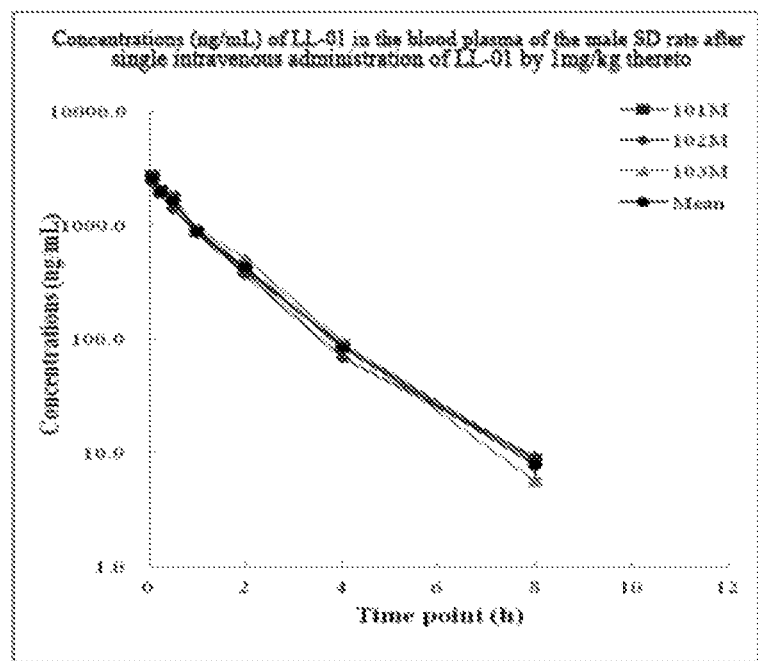
FIG. 3 shows drug concentration-time curves in blood plasma of male SD rats after single intravenous administration of LL-01 (1 mg/kg)
Figure 4:
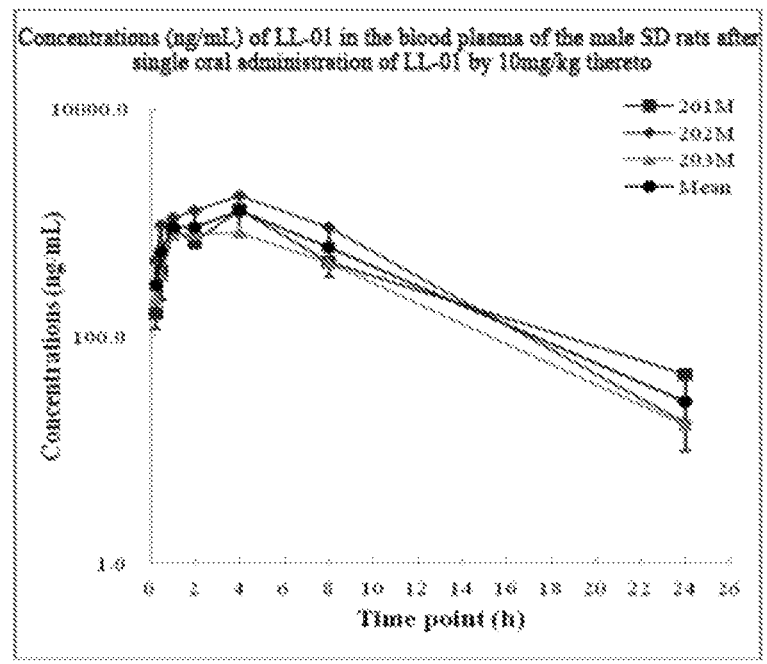
FIG. 4 shows drug concentration-time curves in blood plasma of male SD rats after single oral administration of LL-01 (10 mg/kg).

Drug concentration-time curves in the blood plasma of the male SD rats after single intravenous administration of LL-01 (1 mg/kg) to time are shown in FIG. 3;

Drug concentration-time curves in the blood plasma of the male SD rats after single oral administration of LL-01 (10 mg/kg) thereto are shown in FIG. 4.

The invention claimed is:

1. An indenopyrazole small-molecule tubulin inhibitor, having a structure represented by general formula I:

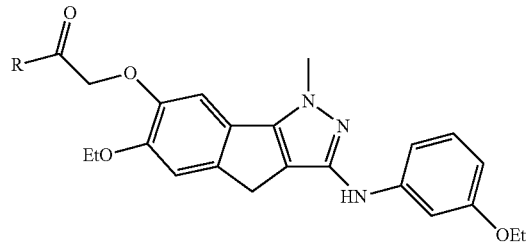

General Formula I wherein R represents $NH_2$ or NHOH.

2. A preparation method of the indenopyrazole small-molecule tubulin inhibitor of claim 1, comprising the following steps:
   using 5-ethoxy-6-hydroxy-1-indenone as a starting raw material, and protecting the 6-site hydroxyl group with a tert-butyldimethylsilyl to obtain 5-ethoxy-6-tert-butyldimethylsiloxy-1-indenone, wherein a mass ratio of the added 5-ethoxy-6-hydroxy-1-indenone to the added tert-butyldimethylchlorosilane is 3.2:3.76;
   reacting the 5-ethoxy-6-tert-butyldimethylsiloxy-1-indenone with 3-ethoxyphenylisothiocyanate for electrophilic addition, and then reacting the obtained product with methylhydrazine for addition-elimination to obtain an indenopyrazole parent nucleus, wherein an addition ratio of the 5-ethoxy-6-tert-butyldimethylsiloxy-1-indenone to the 3-ethoxyphenylisothiocyanate to the methylhydrazine is 4.65 g:3.17 g:4 mL;
   reacting N-(3-ethoxyphenyl)-1H,4H-6-ethoxy-7-tert-butyldimethylsiloxy-1-methylindeno [1,2-c] pyrazole-3-amine, after a protecting group on a 6-site hydroxyl group thereof is removed, with methyl chloroacetate for Williamson ether formation to obtain methyl 2-(6- ethoxy-3-(3-ethoxyphenylamino)-1-methyl-1,4-dihydroindeno[1,2-c]pyrazol-7-yl)acetate, and finally, ammonolysis of the ester group on the methyl 2-(6-ethoxy-3-(3-ethoxyphenylamino)-1-methyl-1,4-dihydroindeno[1,2-c]pyrazol-7-yl)acetate with different amino substituent groups, thereby obtaining the compound of general formula I.

3. A preparation method of the indenopyrazole small-molecule tubulin inhibitor of claim 1, wherein the preparation method is specifically as follows when R represents $NH_2$:

(1) dissolving 5-ethoxy-6-hydroxy-1-indenone into N,N-dimethylformamide, adding imidazole thereto, stirring, and then adding tert-butyldimethylchlorosilane thereto, and stirring; adding citric acid thereto, carrying out cooling, suction filtration, and drying, thereby obtaining 5-ethoxy-6-tert-butyldimethylsiloxy-1-indenone, wherein the mass ratio of the added 5-ethoxy-6-hydroxy-1-indenone to the added imidazole to the added tert-butyldimethylchlorosilane is 3.2:1.7:3.76;

(2) dissolving the 5-ethoxy-6-tert-butyldimethylsiloxy-1-indenone into anhydrous tetrahydrofuran, performing cooling to −78° C., dropwise adding lithium bis(trimethylsilyl) amide thereto, stirring for 2 h, and then increasing the temperature to −45° C. in 45 min, adding 3-ethoxyphenylisothiocyanate already dissolved into anhydrous tetrahydrofuran thereto, stirring at a room temperature, and placing the mixture over night; adding glacial acetic acid thereto, stirring, removing the solvent by evaporating, and carrying out extracting using dichloromethane, washing, and drying using anhydrous sodium sulfate to obtain a crude product of 5-ethoxy-6-tert-butyldimethylsiloxy-2-(3-ethoxyphenylaminothioformyl)-1-indenone, wherein the mass ratio of the 5-ethoxy-6-tert-butyldimethylsiloxy-1-indenone to the 3-ethoxyphenylisothiocyanate is 4.65:3.17;

(3) dissolving the crude product of 5-ethoxy-6-tert-butyldimethylsiloxy-2-(3-ethoxyphenylaminothioformyl)-1-indenone obtained in step (2) into a mixed solvent of dioxane, and ethanol, adding methylhydrazine thereto at 0° C., stirring, and reacting at the room temperature for 84 h; removing the solvent by evaporating, and carrying out column chromatography to obtain N-(3-ethoxyphenyl)-1H,4H-6-ethoxy-7-tert-butyldimethylsiloxy-1-methylindeno [1,2-c] pyrazole-3-amine;

(4) dissolving the N-(3-ethoxyphenyl)-1H,4H-6-ethoxy-7-tert-butyldimethylsiloxy-1-methylindeno [1,2-c] pyrazole-3-amine into tetrahydrofuran, adding tetrabutylammonium fluoride thereto, and stirring; and then carrying out extracting using ethyl acetate, washing, drying using anhydrous sodium sulfate, removing the solvent by evaporating, and column chromatography to obtain N-(3-ethoxyphenyl)-1H,4H-6-ethoxy-7-hydroxy-1-methylindeno [1,2-c] pyrazole-3-amine, wherein the mass ratio of the added N-(3-ethoxyphenyl)-1H,4H-6-ethoxy-7-tert-butyldimethylsiloxy-1-methylindeno [1,2-c] pyrazole-3-amine to the added tetrabutylammonium fluoride is 3.91:2.63;

(5) dissolving the N-(3-ethoxyphenyl)-1H,4H-6-ethoxy-7-hydroxy-1-methylindeno [1,2-c] pyrazole-3-amine into acetone, stirring, adding methyl chloroacetate thereto, reacting at 65° C., and placing the reaction product over night; and then carrying out extracting using ethyl acetate, washing, drying using anhydrous sodium sulfate, and column chromatography to obtain methyl 2-(6-ethoxy-3-(3-ethoxyphenylamino)-1-methyl-1,4-dihydroindeno[1,2-c]pyrazol-7-yl)acetate, wherein the addition ratio of the N-(3-ethoxyphenyl)-1H,4H-6-ethoxy-7-hydroxy-1-methylindeno [1,2-c] pyrazole-3-amine to the methyl chloroacetate is 1.1 g:0.55 ml; and (6) dissolving the methyl 2-(6-ethoxy-3-(3-ethoxyphenylamino)-1-methyl-1,4-dihydroindeno[1,2-c]pyrazol-7-yl)acetate into methanol, adding ammonia water thereto, and reacting at 65° C. for 12 h to obtain 2-(6-ethoxy-3-(3-ethoxyphenylamino)-1-methyl-1,4-dihydroindeno[1,2-c]pyrazol-7-yl)acetamide, wherein the addition ratio of the methyl 2-(6-ethoxy-3-(3-ethoxyphenylamino)-1-methyl-1,4-dihydroindeno[1,2-c]pyrazol-7-yl)acetate to the ammonia water is 15 g:52 mL.

4. A preparation method of the indenopyrazole small-molecule tubulin inhibitor of claim 1, wherein the preparation method is specifically as follows when R represents NHOH:

(1) dissolving 5-ethoxy-6-hydroxy-1-indenone into N,N-dimethylformamide, adding imidazole thereto, stirring, and then adding tert-butyldimethylchlorosilane thereto, and stirring; adding citric acid thereto, carrying out cooling, suction filtration, and vacuum drying, thereby obtaining 5-ethoxy-6-tert-butyldimethylsiloxy-1-indenone, wherein the mass ratio of the added 5-ethoxy-6-hydroxy-1-indenone to the added imidazole to the added tert-butyldimethylchlorosilane is 3.2:1.7:3.76;

(2) dissolving the 5-ethoxy-6-tert-butyldimethylsiloxy-1-indenone into anhydrous tetrahydrofuran, performing cooling to −78° C., dropwise adding lithium bis(trimethylsilyl) amide thereto, stirring for 2 h, and then increasing the temperature to −45° C. in 45 min, adding 3-ethoxyphenylisothiocyanate already dissolved into anhydrous tetrahydrofuran thereto, stirring at a room temperature, and placing the mixture over night; adding glacial acetic acid thereto, stirring, removing the solvent by evaporating, and carrying out extracting using dichloromethane, washing, and drying using anhydrous sodium sulfate to obtain a crude product of 5-ethoxy-6-tert-butyldimethylsiloxy-2-(3-ethoxyphenylaminothioformyl)-1-indenone, wherein the mass ratio of the 5-ethoxy-6-tert-butyldimethylsiloxy-1-indenone to the 3-ethoxyphenylisothiocyanate is 4.65:3.17;

(3) dissolving the crude product of 5-ethoxy-6-tert-butyldimethylsiloxy-2-(3-ethoxyphenylaminothioformyl)-1-indenone obtained in step (2) into a mixed solvent of dioxane and ethanol, adding methylhydrazine thereto at 0° C., stirring, and reacting at the room temperature for 84 h; removing the solvent by evaporating, and carrying out column chromatography to obtain N-(3-ethoxyphenyl)-1H,4H-6-ethoxy-7-tert-butyldimethylsiloxy-1-methylindeno [1,2-c] pyrazole-3-amine;

(4) dissolving the N-(3-ethoxyphenyl)-1H,4H-6-ethoxy-7-tert-butyldimethylsiloxy-1-methylindeno [1,2-c] pyrazole-3-amine into tetrahydrofuran, adding tetrabutylammonium fluoride thereto, and stirring for 1 h; and then carrying out extracting using ethyl acetate, washing, drying using anhydrous sodium sulfate, and column chromatography to obtain N-(3-ethoxyphenyl)-1H,4H-6-ethoxy-7-hydroxy-1-methylindeno [1,2-c] pyrazole-3-amine, wherein the mass ratio of the added N-(3-ethoxyphenyl)-1H,4H-6-ethoxy-7-tert-butyldimethylsiloxy-1-methylindeno [1,2-c] pyrazole-3-amine to the added tetrabutylammonium fluoride is 3.91:2.63;

(5) dissolving the N-(3-ethoxyphenyl)-1H,4H-6-ethoxy-7-hydroxy-1-methylindeno [1,2-c] pyrazole-3-amine into acetone, stirring, adding methyl chloroacetate thereto, reacting at 65° C., and placing the reaction product over night; and then carrying out extracting using ethyl acetate, washing, drying using anhydrous sodium sulfate, and column chromatography to obtain methyl 2-(6-ethoxy-3-(3-ethoxyphenylamino)-1-methyl-1,4-dihydroindeno[1,2-c]pyrazol-7-yl)acetate, wherein the addition ratio of the N-(3-ethoxyphenyl)-1H,4H-6-ethoxy-7-hydroxy-1-methylindeno [1,2-c] pyrazole-3-amine to the methyl chloroacetate is 1.1 g:0.55 ml; and (6) dissolving hydroxylamine hydrochloride into methanol, adding sodium methoxide thereto for neutralization, adding the alcoholic solution of the hydroxylamine to the obtained methanol solution of the methyl 2-(6-ethoxy-3-(3-ethoxyphenylamino)-1-methyl-1,4-dihydroindeno[1,2-c]pyrazol-7-yl)acetate, and reacting at 65° C. for 6 h to obtain 2-(6-ethoxy-3-(3-ethoxyphenylamino)-1-methyl-1,4-dihydroindeno[1,2-c]pyrazol-7-yl)-N-hydroxyacetamide, wherein a volume ratio of the alcoholic solution of the hydroxylamine to the methanol solution of the methyl 2-(6-ethoxy-3-(3-ethoxyphenylamino)-1-methyl-1,4-dihydroindeno[1,2-c]pyrazol-7-yl)acetate is 1:4.

5. A method comprising: administering an anti-tumor drug comprising the indenopyrazole small-molecule tubulin inhibitor of claim 1 to a subject in need thereof.

6. The method of claim 5, wherein the anti-tumor drug is administered to treat one or more members selected from the group consisting of hepatocellular carcinoma, prostate carcinoma, cervical carcinoma, breast adenocarcinoma, and leukemia.

7. An anti-tumor pharmaceutical preparation, containing an effective quantity of the indenopyrazole small-molecule tubulin inhibitor having the structure of general formula I of claim 1.

8. The pharmaceutical preparation of claim 7, which may be produced with one or more pharmaceutically acceptable carriers and/or excipients into an oral preparation or a parenteral administration preparation.

9. The pharmaceutical preparation of claim 8, wherein
the carriers are selected from the group consisting of normal saline, buffered saline, glucose, water, glycerol, ethanol, and combinations thereof; and
the excipients are selected from the group consisting of calcium phosphate, magnesium stearate, talcum powder, dextrin, starch, gel cellulose, methylcellulose, carboxymethylcellulose sodium salt, and polyvinylpyrrolidone.

* * * * *